United States Patent
Yuan et al.

[11] Patent Number: 5,681,312
[45] Date of Patent: Oct. 28, 1997

[54] SPINE CONSTRUCT WITH BAND CLAMP

[75] Inventors: Hansen A. Yuan, Fayetteville, N.Y.; Edward C. Benzel, Albuquerque, N. Mex.; Alex Dinello, Palo Alto, Calif.; Michael H. Wefers, South Euclid, Ohio; Aaron C. Smith, Gibsonia, Pa.

[73] Assignee: AcroMed Corporation, Cleveland, Ohio

[21] Appl. No.: 660,689

[22] Filed: May 31, 1996

[51] Int. Cl.$^6$ ................................. A61B 17/70
[52] U.S. Cl. .............................. 606/61; 606/72
[58] Field of Search ..................... 606/61, 60, 72, 606/73

[56] References Cited

U.S. PATENT DOCUMENTS

| | | |
|---|---|---|
| 4,041,939 | 8/1977 | Hall . |
| 4,648,388 | 3/1987 | Steffee . |
| 5,147,360 | 9/1992 | Dubousset . |
| 5,152,303 | 10/1992 | Allen . |
| 5,261,911 | 11/1993 | Carl . |
| 5,403,314 | 4/1995 | Currier . |
| 5,487,742 | 1/1996 | Coates et al. . |
| 5,498,262 | 3/1996 | Bryan . |
| 5,522,816 | 6/1996 | Dinello et al. ............ 606/61 |

OTHER PUBLICATIONS

AcroMed Corporation catalog discloses anterior spinal instrumentation. no date.

Primary Examiner—Michael Buiz
Assistant Examiner—Daphna Shai
Attorney, Agent, or Firm—Tarolli, Sundheim, Covell, Tummino & Szabo

[57] ABSTRACT

An apparatus for retaining first and second vertebrae of a spinal column in a desired spatial relationship comprises first and second longitudinal members positionable along the spinal column. A first member connects the first and second longitudinal members to the first vertebra and second member connects the first and second longitudinal members to the second vertebra. A connector for interconnecting the first and second longitudinal members extends between the first and second longitudinal members and transverse to the first and second longitudinal members. The connector includes a band defining first and second openings through which the first and second longitudinal members are extendable. The band includes first and second portions movable relatively between a first position in which the first and second band portions clamp the first and second longitudinal members in said first and second openings and a second position in which the first and second band portions are released from clamping the longitudinal members in said first and second openings.

13 Claims, 3 Drawing Sheets

SPINE CONSTRUCT WITH BAND CLAMP

BACKGROUND OF THE INVENTION

The present invention relates to an apparatus for use in retaining bone portions in a desired spatial relationship. Specifically, the present invention relates to a connector for interconnecting longitudinal members which are extensible along a spinal column and connectable to vertebrae to retain the vertebrae in a desired spatial relationship.

A known connector for interconnecting longitudinal members of an apparatus for retaining first and second vertebrae of a spinal column in a desired spatial relationship is disclosed in U.S. Pat. No. 5,487,742. U.S. Pat. No. 5,487,742 discloses one example of many such connectors.

SUMMARY OF THE INVENTION

The present invention is an apparatus for retaining first and second vertebrae of a spinal column in a desired spatial relationship. In one embodiment of the invention, the apparatus comprises first and second longitudinal members positionable along the spinal column. The apparatus further includes a first means for connecting the first and second longitudinal members to the first vertebrae and second means for connecting the first and second longitudinal members to the second vertebrae. A connector for interconnecting the first and second longitudinal members includes first and second openings through which the first and second longitudinal members are extendable. The first and second openings are defined by a one piece band having first and second portions which are movable relative to each other between a first position in which the first and second portions clamp the first and second longitudinal members in the first and second openings and a second position in which the first and second portions are released from the longitudinal members.

In another embodiment of the invention, a plate has a body portion and an integral band portion. The body portion of the plate has an opening for receiving a fastener for securing the body portion to a bone. The band portion defines an opening through which a member which lies along the bone may extend. A fastener clamps the band portion around the member to connect the member to the body portion of the plate.

BRIEF DESCRIPTION OF THE DRAWINGS

The foregoing and the other features of the present invention will become more apparent to one skilled in the art upon reading the following description of the present invention with reference to the accompanying drawings, wherein.

DESCRIPTION OF PREFERRED EMBODIMENTS OF THE INVENTION

Figure 1:
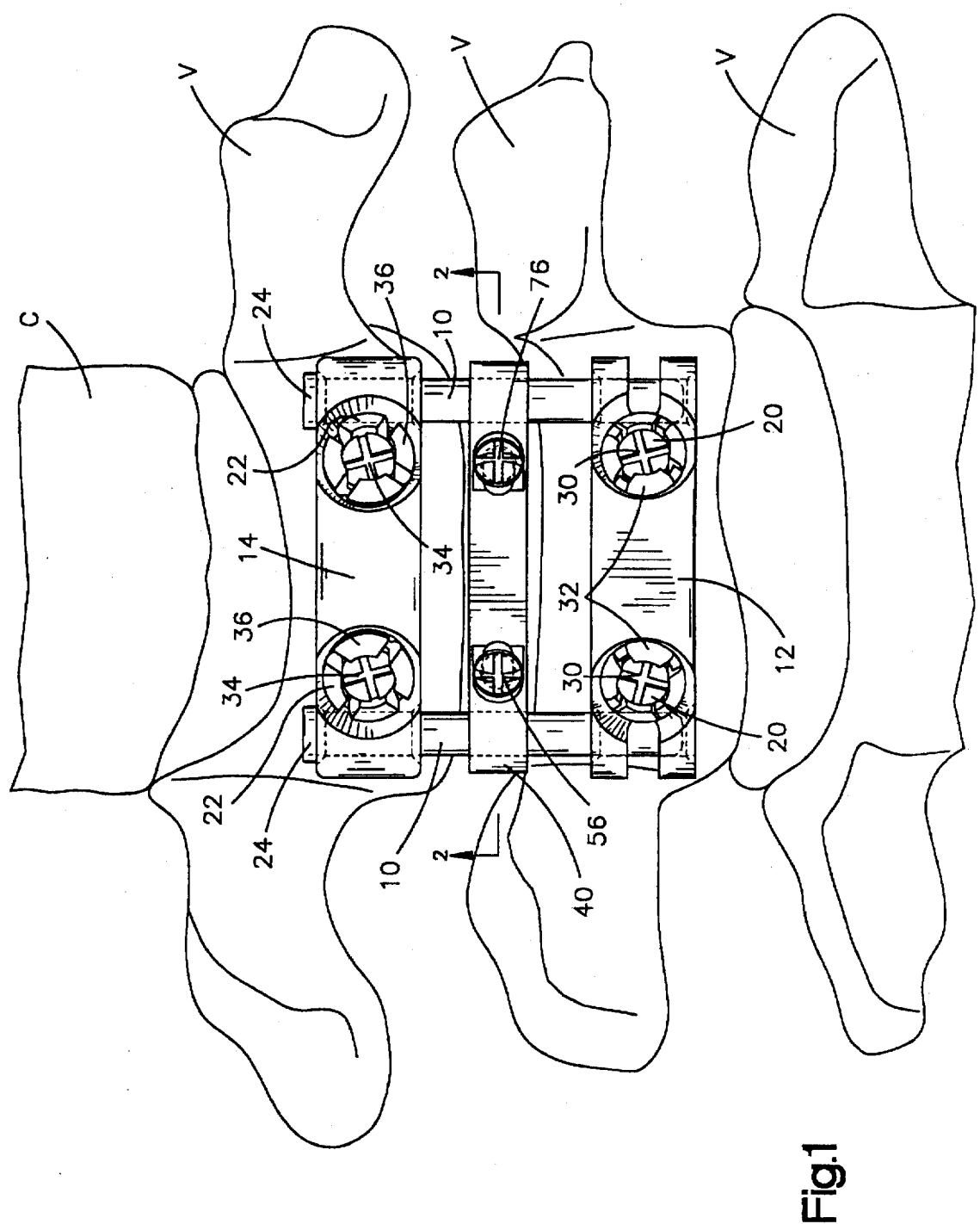
FIG. 1 is a view of a cervical portion of a spinal column with an apparatus constructed in accordance with the present invention connected to an anterior portion of cervical vertebrae to retain a desired spatial relationship between the cervical vertebrae of the spinal column.

A pair of surgically implantable rods 10 (FIG. 1) for stabilizing a human spinal column C are connected with cervical vertebrae V of the spinal column by plates 12 and 14. The plates 12 and 14 have openings through which the rods 10 extend. Each rod 10 is elongate and has a circular cross-section taken in a plane extending perpendicular to the longitudinal central axis of the rod. The rod 10 is bendable to conform to a desired curvature of the spinal column C. The rods 10 have sufficient length and rigidity to maintain the vertebrae V in the desired relationship. The rods 10 are made of a biocompatible material such as titanium or stainless steel.

Each of the rods 10 has a length which is at least sufficient to enable the rod to span at least two of the cervical vertebrae V. In the embodiment of the invention illustrated in FIG. 1, the rods 10 span two vertebrae V. Of course, the length of the rods 10 will depend upon the condition to be corrected and the number of vertebrae V to be held in a desired spatial relationship relative to each other by the rods 10.

The plate 12 is connected to a vertebra V by fasteners 20. The fasteners 20 also fix the rods 10 relative to the plate 12 to prevent relative movement between the rods 10 and the plate 12. The plate 14 is connected to a vertebra V by fasteners 22. The fasteners 22 permit relative movement between the plate 14 and the rods 10. Each of the rods 10 terminates in a cap 24 engageable with the plate 14. The caps 24 prevent movement of the plate 14 relative to the rods 10 in a direction away from the plate 12, while allowing movement of the plate 14 in a direction toward the plate 12.

Each of the fasteners 20 preferably includes an expander 30 for expanding a head end portion 32 of the fastener 20. The expander 30 expands the head end portion 32 into engagement with a surface defining an opening in the plate 12 through which the fastener 20 extends. The head end portion 32 also expands into engagement with the rod 10 to clamp the rod to the plate 12. Accordingly, the fastener 20 prevents relative movement between the plate 12, the fastener 20 and the rod 10. Although the fastener 20 clamps the rod 10 to the plate 12, the rod may be fixed to the plate in any manner.

Each of the fasteners 22 preferably has an expander 34 for expanding a head end portion 36 of the fastener 22. The expander 34 expands the head end portion 36 into engagement with a surface defining an opening in the plate 14 through which the fastener 22 extends. Accordingly, each fastener 22 is prevented from moving relative to the plate 14. However, the plate 14 is movable relative to the rods 10.

A one piece band clamp 40 (FIGS. 1 and 2) for interconnecting the rods 10 extends between the rods and transverse to the rods. The band 40 is made of a suitable biocompatible material such as titanium or stainless steel. The band 40 circumscribes the rods 10. The band 40 (FIGS. 2–4) includes a lower band portion 42, as viewed in FIGS. 2 and 3, and an upper band portion 44 extending generally parallel to each other. The upper and lower band portions 42 and 44 define first and second openings 46 and 48 through which the rods 10 extend.

The opening 46 is defined by a first side portion 50 of the lower band portion 42 and a first side portion 52 of the upper band portion 44. The first side portion 50 of the lower portion 42 defining the opening 46 has a threaded opening 54 for threadably receiving a fastener 56.

The first side portion 52 of the upper band portion 44 defining the opening 46 has an opening 58 through which the fastener 56 extends. The opening 58 is partially defined by a cylindrical surface 60 which extends parallel to an axis of the opening 58. The opening 58 is also partially defined by a recess 62 in the band 40. The recess 62 and the cylindrical surface 60 define a shoulder 64 in the opening 58 against which a head 66 of the screw 56 engages.

Figure 2:
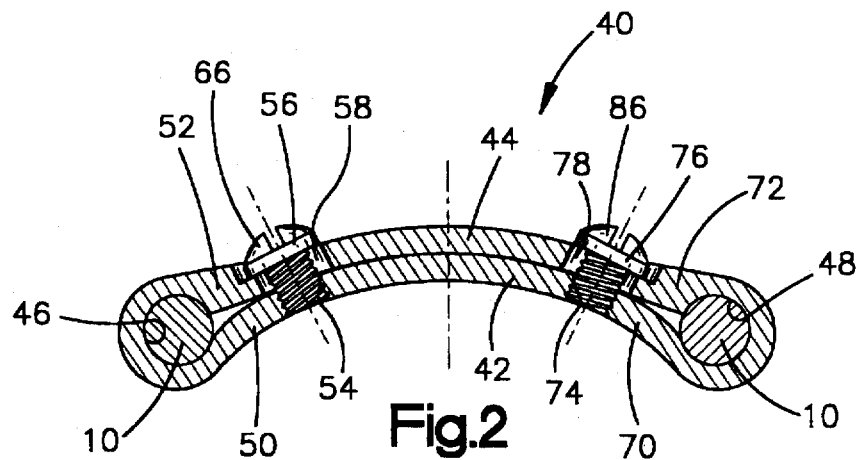
FIG. 2 is an enlarged sectional view, taken generally along the line 2—2 of FIG. 1.
Figure 3:
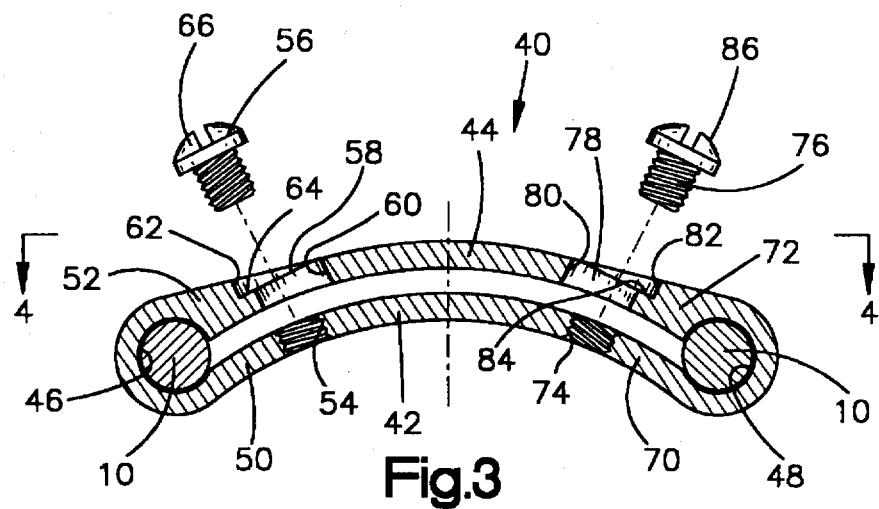
FIG. 3 is an exploded view of the parts of FIG. 2.
Figure 4:
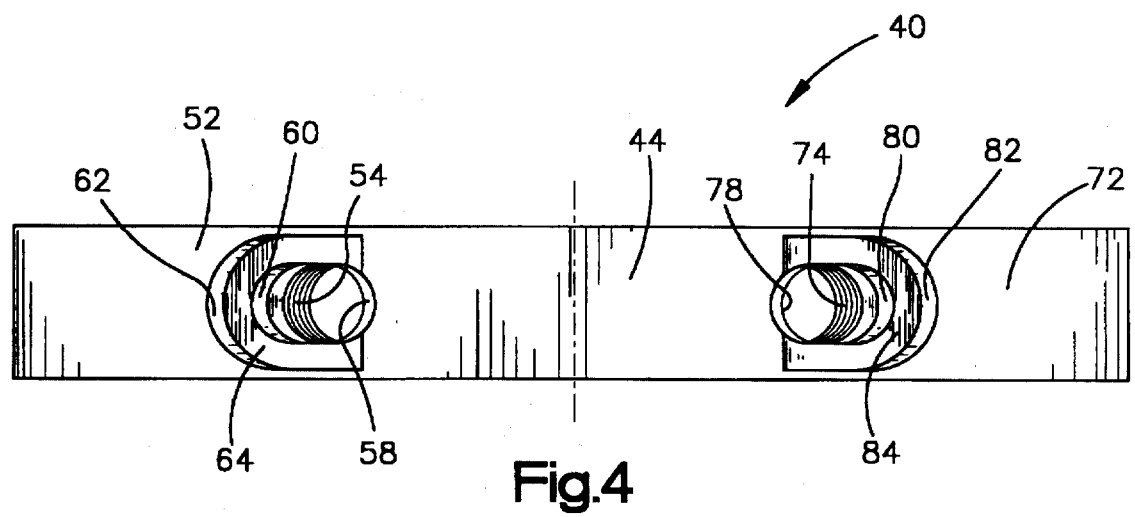
FIG. 4 is an enlarged plan view taken generally along the line 4—4 of FIG. 3.

The axes of the openings 54 and 58 are offset from each other when the band 40 is in a released condition, as shown in FIG. 3. As the fastener 56 is threaded into the opening 54 and the portions 50, 52 move from their positions shown in FIG. 3 to the positions shown in FIG. 2, the portions pivot around the rod 10 and the axes of the openings 54 and 58 become aligned.

The opening 48 is defined by a second side portion 70 of the lower band portion 42 and a second side portion 72 of the upper band portion 44. The first side portion 50 of the lower band portion 42 is integral with the second side portion 70. The first side portion 52 of the upper band portion 44 is integral with the second side portion 72. The second side portion 70 of the lower portion 42 has a threaded opening 74 for threadably receiving a fastener 76.

The second side portion 72 defining the opening 48 has an opening 78 through which the fastener 76 extends. The opening 78 is partially defined by a cylindrical surface 80 which extends parallel to an axis of the opening 78. The opening 78 is partially defined by a recess 82 in the portion 72. The cylindrical surface 80 and the recess 82 define a shoulder 84 against which a head 86 of the screw 76 engages.

The axes of the openings 74 and 78 are offset from each other when the band 40 is in a released condition as shown in FIG. 3. As the fastener 76 is threaded into the opening 74 and the portions 70, 72 move from the positions shown in FIG. 3 to the positions shown in FIG. 2, the portions 70, 72 pivot around the rod 10 into engagement so that the axes of the openings 74 and 78 are aligned.

When the rods 10 are to be connected to the vertebrae V, the rods are placed through the openings in the plates 12 and 14 and through the openings 46 and 48 in the band 40. The inherent resiliency of the band 40 positions portions 50, 52 and 70, 72 so that the rods may be easily positioned in the openings 46 and 48 in the band 40. The plates 12 and 14 are positioned on the vertebrae V and the fasteners 20 and 22 are threaded into the vertebrae to connect the plates 12 and 14 to the vertebrae. The fasteners 56 and 76 are threaded into the openings 54 and 74. Accordingly, the portions 50 and 52 clamp one of the rods 10 in the opening 46 and the portions 70 and 72 clamp the other rod in the opening 48. The band clamp 40 is thus fixedly clamped to the rods 10 and securely interconnects the rods 10. The band 40 may be released from the rods 10 by loosening the fasteners 56, 76. As the fasteners 56, 76 are loosened, the inherent resiliency of the band 40 causes the portions 50, 52 and 70, 72 to release their clamping force on the rods 10.

Figure 5:
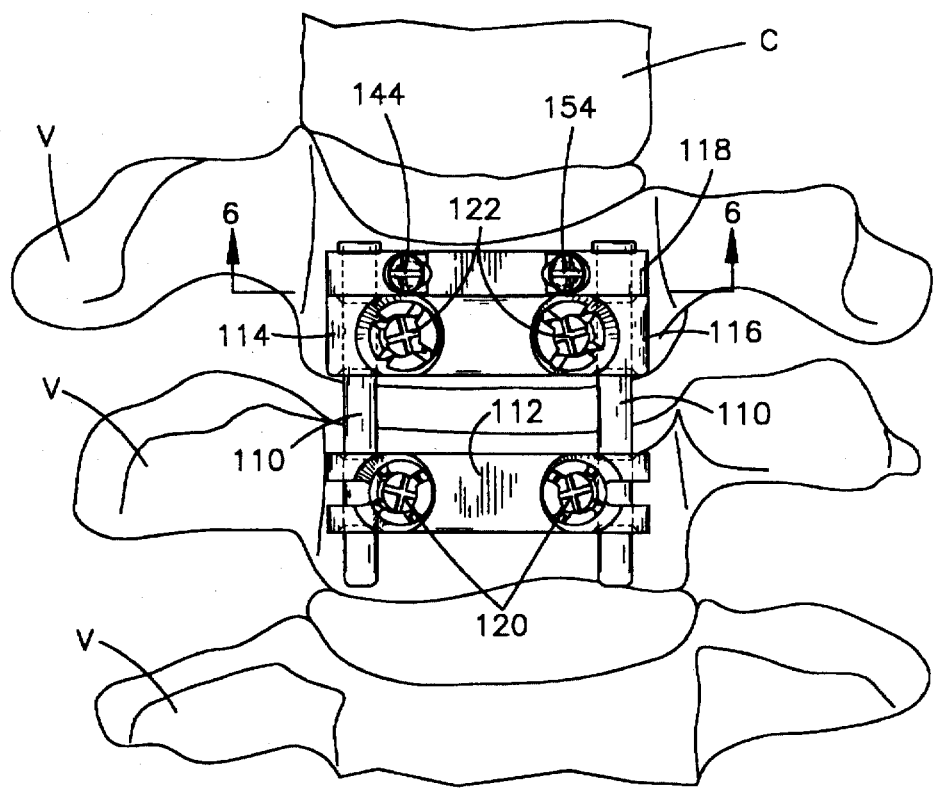
FIG. 5 is a view of a cervical portion of a spinal column with a second embodiment of an apparatus constructed in accordance with the present invention connected to an anterior portion of cervical vertebrae to retain a desired spatial relationship between the cervical vertebrae of the spinal column.

In a second embodiment of the present invention, rods 110 (FIG. 5) for stabilizing a human spinal column C are connected to anterior portions of cervical vertebra V of the spinal column by plates 112 and 114. The plate 112 is connected to a vertebra V by fasteners 120. The fasteners 120 also fix the rods 110 relative to the plate 112 to prevent relative movement between the rods 110 and the plate 112.

The plate 112 and the fasteners 120 are identical to the plate 12 and the fasteners 20 described in connection with FIG. 1. Therefore, the plate 112 and the fasteners 120 will not be described in detail.

The plate 114 has a body portion 116 and a band portion 118 integral with the body portion. The plate 114 is connected to a vertebra by fasteners 122. The fasteners 122 are identical to the fasteners 22 described in connection with FIG. 1. Therefore, the fasteners 122 will not be described in detail.

The plate 114 has a surface 130 for facing the vertebra V. The surface 130 extends along the body portion 116 and the band portion 118. The body portion 116 of the plate 114 is substantially similar to the plate 14 disclosed in FIG. 1, and therefore, will not be described in detail. The band portion 118 of the plate 114 circumscribes the rods 110 and is substantially similar to the band 40 described in connection with FIGS. 1–4. Therefore, the band portion 118 will not be described in detail.

Figure 6:
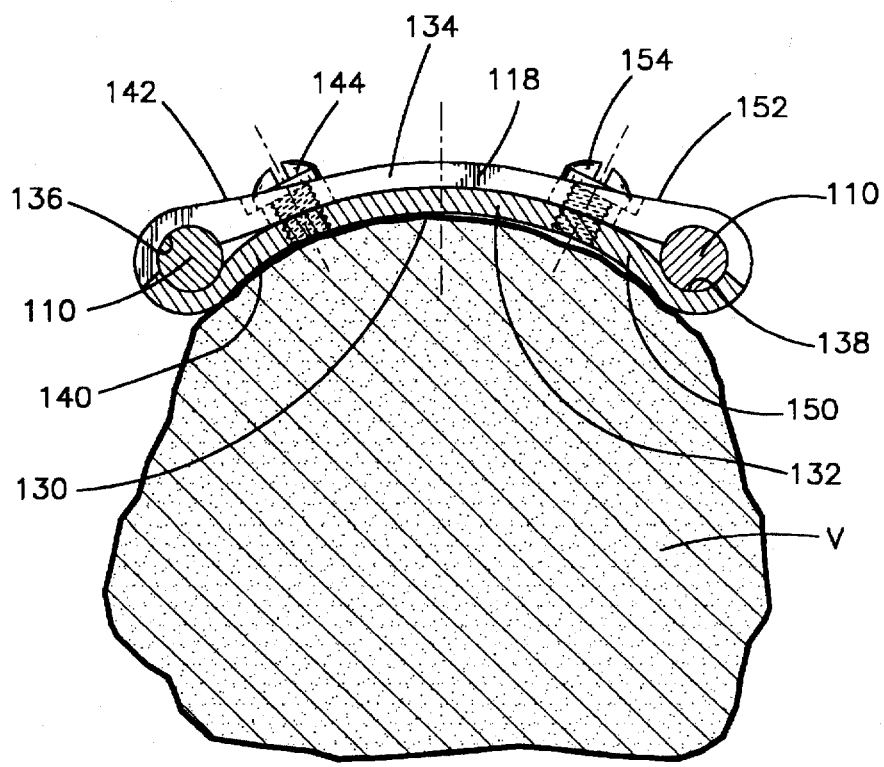
FIG. 6 is a sectional view, taken generally along the line 6—6 of FIG. 5.

The band portion 118 has a lower portion 132, as viewed in FIG. 6, and an upper portion 134. The upper and lower portions define first and second openings 136 and 138 for receiving the rods 110. The opening 136 is defined by a first side portion 140 of the lower portion 132 and a first side portion 142 of the upper portion 134. The portion 140 of the lower portion 132 has a threaded opening for receiving a fastener 144. The portion 142 of the upper portion 134 has an opening through which the fastener extends. The fastener 144 threadably engages the opening in the portion 140 of the lower portion 132 to cause the portion 142 of the upper portion 134 to move toward the portion 140 and clamp the rod 110 in the opening 136. The fastener 144 overcomes the inherent resiliency of the band portion 118 to cause the clamping of the rod 100 in the opening 136.

The opening 138 is defined by a second side portion 150 of the lower portion 132 and a second side portion 152 of the upper portion 134. The first and second side portions 140 and 150 of the lower portion 132 are integral with the body portion 116 of the plate 114. The first side portion 142 of the upper portion 134 is integral with the second side portion 152. The second side portion 150 of the lower portion 132 has a threaded opening for receiving a fastener 154. The second side portion 152 of the upper portion 134 has an opening through which the fastener 154 extends. The fastener 154 threadably engages the opening in the portion 150 to cause the portion 152 to move toward the portion 150 and clamp the rod 110 in the opening 138. The fastener 154 overcomes the inherent resiliency of the band portion 118 to cause the clamping of the rod 110 in the opening 136.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for retaining first and second vertebrae of a spinal column in a desired spatial relationship, said apparatus comprising:
   first and second longitudinal members positionable along the spinal column;
   first means for connecting said first and second longitudinal members to the first vertebra;
   second means for connecting said first and second longitudinal members to the second vertebra; and
   a connector for interconnecting said first and second longitudinal members;

said connector including first and second openings through which said first and second longitudinal members are extendable, said first and second openings being defined by a one piece band having first and second portions movable relatively between a first position in which said first and second band portions clamp the first and second longitudinal members in said first and second openings and a second position in which said first and second band portions are released from clamping said longitudinal members in said first and second openings.

2. An apparatus as set forth in claim 1 wherein said first band portion has a threaded opening and said second band portion has an opening aligned with said threaded opening, said apparatus further including a fastener for threadably engaging said threaded opening in said first band portion and extending through said opening in said second band portion to move said first and second band portions to their first positions.

3. An apparatus as set forth in claim 2 wherein said first band portion engages said second band portion when said first and second band portions are in their first positions.

4. An apparatus as set forth in claim 1 wherein said first means for connecting said first and second longitudinal members to the first vertebra includes a member having an opening for receiving a fastener to connect said member to the first bone portion, said member being connectable with said first and second longitudinal members, said first band portion being integral and fixedly connected with said member.

5. An apparatus for retaining first and second vertebrae of a spinal column in a desired spatial relationship, said apparatus comprising:

first and second longitudinal members positionable along the spinal column;

first means for connecting said first and second longitudinal members to the first vertebra;

second means for connecting said first and second longitudinal members to the second vertebra;

said first means comprising a one piece plate having a body portion having first openings through which said longitudinal members extend and at least one fastener for connecting said body portion to the first vertebra, said plate further having a band portion integral and fixedly connected with said body portion, said band portion defining at least one opening through which one of said longitudinal members extends, said band portion encircling said one of said longitudinal members; and a second fastener for clamping said band portion around said one of said longitudinal members to connect said one of said longitudinal members to said body portions.

6. An apparatus as set forth in claim 5 wherein said band portion defines first and second openings through which said first and second longitudinal members extend, said band portion encircling said first and second longitudinal members.

7. An apparatus as set forth in claim 5 wherein said band portion includes first and second portions defining said opening through which said longitudinal member extends, said first portion including a threaded opening for threadably engaging said second fastener, said second portion having an opening through which said second fastener extends.

8. An apparatus comprising:

a pair of longitudinal members positionable along a spinal column;

a plate having openings through which said longitudinal members are extendable and connectable to the spinal column to connect said longitudinal members to the spinal column;

a one piece band having first and second openings through which said longitudinal members extend, said first opening being defined by first and second portions of said band, said second opening being defined by third and fourth portions of said band; and fastener means for clamping said band against said longitudinal members.

9. An apparatus as set forth in claim 8 wherein said first portion of said band is integral and fixedly connected with said third portion.

10. An apparatus as set forth in claim 9 wherein said second portion of said band is integral and fixedly connected with said fourth portion.

11. An apparatus as set forth in claim 9 wherein said first and third portions of said band are integral and fixedly connected with said plate.

12. An apparatus as set forth in claim 8 wherein said fastener means comprises first and second fasteners, said first portion having a first threaded opening for threadably receiving said first fastener, said second portion having a second opening aligned with said first threaded opening through which said first fastener extends, said third portion having a third threaded opening for threadably receiving said second fastener, said fourth portion having a fourth opening aligned with said third opening through which said second fastener extends.

13. Apparatus comprising:

a plate having a body portion and a band portion integral and fixedly connected with said body portion;

said body portion having an opening for receiving a fastener for securing said body portion to a bone;

said band portion defining an opening through which a member which lies along the bone may extend; and a fastener for clamping said band portion around said member to connect said member and said body portion, said fastener including a threaded fastener, said band portion including first and second portions defining the opening through which said member extends, said first portion having a threaded opening for threadably receiving said fastener, said second portion having an opening through which said fastener extends.

* * * * *